US010052296B2

(12) United States Patent
Khurana et al.

(10) Patent No.: US 10,052,296 B2
(45) Date of Patent: Aug. 21, 2018

(54) FORMULATIONS FOR TREATING PAIN

(71) Applicant: Nevakar Inc., Bridgewater, NJ (US)

(72) Inventors: Varun Khurana, Raritan, NJ (US); Vivek Yadav, Henderson, NV (US); Jack Martin Lipman, West Milford, NJ (US); Tao Zhang, Towaco, NJ (US); Iouri V. Ilitchev, Hillsborough, NJ (US); Tushar Hingorani, Bridgewater, NJ (US); Kumaresh Soppimath, Plainsboro, NJ (US); Navneet Puri, Lebanon, NJ (US)

(73) Assignee: NEVAKAR INC., Bridgewater, NJ (US)

( * ) Notice: Subject to any disclaimer, the term of this patent is extended or adjusted under 35 U.S.C. 154(b) by 0 days.

(21) Appl. No.: 15/482,196

(22) Filed: Apr. 7, 2017

(65) Prior Publication Data

US 2017/0290793 A1    Oct. 12, 2017

Related U.S. Application Data

(60) Provisional application No. 62/319,526, filed on Apr. 7, 2016.

(51) Int. Cl.
*A61K 31/195* (2006.01)
*A61K 9/00* (2006.01)
*A61K 31/167* (2006.01)
*A61K 45/06* (2006.01)

(52) U.S. Cl.
CPC .......... *A61K 31/195* (2013.01); *A61K 9/0019* (2013.01); *A61K 31/167* (2013.01); *A61K 45/06* (2013.01)

(58) Field of Classification Search
CPC .... A61K 31/195; A61K 45/06; A61K 31/167; A61K 9/0019
See application file for complete search history.

(56) References Cited

U.S. PATENT DOCUMENTS

| | | | |
|---|---|---|---|
| 6,426,368 B2 * | 7/2002 | Bueno | A61K 31/195 514/561 |
| 2005/0004219 A1 * | 1/2005 | Hildebrand | A61K 31/197 514/561 |

FOREIGN PATENT DOCUMENTS

| | | |
|---|---|---|
| EP | 2 151 237 A1 | 2/2010 |
| WO | 1999/008670 A1 | 5/1999 |
| WO | 2005/044252 A1 | 5/2005 |

OTHER PUBLICATIONS

Durmus et al., "The Post-Operative Analgesic Effects of a Combination of Gabapentin and Paracetamol in Patients Undergoing Abdominal Hysterectomy: A Randomized Clinical Trial", Acta Anaesthesiologica Scandinavica, vol. 21, Jan. 1, 2007, pp. 299-304.
Kusunose et al., "Molecular Bassis for the Dosing Time-Dependency of Anti-Allodynic Effects of Gabapentin in a Mouse Model of Neuropathic Pain", Molecular Pain, Biomed Central, vol. 6, No. 1, Nov. 26, 2010, pp. 1-8.
International Search Report and Written Opinion for corresponding International Application No. PCT/US2017/026640, dated Jun. 12, 2017.

* cited by examiner

*Primary Examiner* — Sudhakar Katakam
(74) *Attorney, Agent, or Firm* — Wilson Sonsini Goodrich & Rosati

(57) ABSTRACT

Formulations, methods of manufacturing, methods of stabilizing, kits, and uses as medicament are provided, for example for the treatment of pain. The formulations can comprise gabapentin optionally combined with at least one non-opioid pain drug in an aqueous carrier. The pharmaceutical formulation can have a pH of about 2.0 to about 10.0. The at least one non-opioid pain drug can be acetaminophen. The components can be included in any amount suitable for purposes of obtaining properties desirable for an injectable infusion, for example an intravenous infusion.

17 Claims, 3 Drawing Sheets

FIGURE 1

Table 2: Stability of GBP in presence of different stabilizers and solvents

| Example | D | | E | | F | | G | | H | | I | | J | | K | | L | | M | | N | | O | | P | |
|---|---|---|---|---|---|---|---|---|---|---|---|---|---|---|---|---|---|---|---|---|---|---|---|---|---|---|
| | Glycine | | Lysine | | Deoxycholic acid | | β-Cyclodextrin | | Sodium oleate | | PVP | | CMC | | L-glutamic acid | | PEG 400 | | Propylene glycol | | Glycerol | | Sorbitol | | Manitol | |
| | 10 | | 10 | | 5 | | 10 | | 0.1 | | 10 | | 10 | | 10 | | 21 | | 4 | | 4.83 | | 9.55 | | 9.55 | |
| Gabapentin | | | | | | | | | | | 9 | | | | | | | | | | | | | | | |
| Sodium Hydroxide | | | | | | | | | | | q.s. pH 5.5 | | | | | | | | | | | | | | | |
| Hydrochloric Acid | | | | | | | | | | | q.s. pH 5.5 | | | | | | | | | | | | | | | |
| Vehicle | | | | | | | | | | | q.s. 1 mL | | | | | | | | | | | | | | | |
| | G | L | G | L | G | L | G | L | G | L | G | L | G | L | G | L | G | L | G | L | G | L | G | L | G | L |
| Assay (T0) (%) | 99.2 | ND | 99.6 | ND | 100.6 | ND | 98.9 | ND | 102.1 | ND | 98.9 | ND | 101.6 | ND | 101.4 | ND | 95.8 | ND | 95.7 | ND | 94.5 | ND | 93.2 | ND | 96.1 | ND |
| Post Sterilization (%) | 96.3 | 3.97 | 96.1 | 4.19 | 93.7 | 7.11 | 92.6 | 6.93 | 95.4 | 4.63 | 95.9 | 3.72 | 92.3 | 7.27 | 60.1 | 34.24 | 89.1 | 4.34 | 90.1 | 4.3 | 91.5 | 4.41 | 90.1 | 4.32 | 90.4 | 4.5 |

G= GBP; L= Lactam; ND= Not Detected

FIGURE 2

Table 10: pH dependent stability studies of APAP+GBP at different pH range (4.0-8.0)

| | Gabapentin | | | | | | | | | | | Acetaminophen | | | | | | | | |
|---|---|---|---|---|---|---|---|---|---|---|---|---|---|---|---|---|---|---|---|---|
| | 25°C/60% RH | | | | | | 40°C/75% RH | | | | | | 25°C/60% RH | | | | 40°C/75% RH | | | |
| | Assay | | | Lactam Impurity | | | Assay | | | Lactam Impurity | | | Assay | | | | Assay | | | |
| | T0 | 1 week | 2 Week | 1 Month | T0 | 1 week | 2 Week | 1 Month | 1 week | 2 week | 1 Month | 1 week | 2 week | 1 Month | T0 | 1 week | 2 week | 1 Month | 1 week | 2 week | 1 Month |
| pH 4.0 | 99.3 | 99.2 | 99.2 | 99.4 | ND | ND | 0.3 | 0.8 | 98.7 | 96.8 | 91.6 | 1.1 | 2.5 | 5.2 | 101.0 | 99.9 | 98.9 | 100.2 | 100.0 | 99.3 | 97.6 |
| pH 4.5 | 99.1 | 100.4 | 99.1 | 98.9 | ND | ND | ND | 0.3 | 99.3 | 99.8 | 97.7 | 0.5 | 1.1 | 2.4 | 100.7 | 100.9 | 99.6 | 99.6 | 100.5 | 99.6 | 99.6 |
| pH 5.0 | 99.6 | 100.5 | 99.8 | 100.3 | ND | ND | ND | ND | 101.0 | 99.1 | 100.5 | 0.18 | 0.4 | 0.9 | 100.0 | 99.8 | 99.9 | 99.8 | 99.4 | 99.9 | 100.6 |
| pH 5.5 | 99.1 | 100.4 | 100.0 | 100.6 | ND | ND | ND | ND | 100.7 | 100.4 | 99.5 | ND | ND | 0.3 | 101.0 | 100.4 | 99.7 | 100.6 | 100.7 | 99.9 | 99.3 |
| pH 6.0 | 98.3 | 98.9 | 100.4 | 100.4 | ND | ND | ND | ND | 99.9 | 100.2 | 99.4 | ND | ND | ND | 100.1 | 100.1 | 99.2 | 100.3 | 100.6 | 100.0 | 99.3 |
| pH 6.5 | 98.5 | 99.7 | 100.1 | 100.2 | ND | ND | ND | ND | 100.2 | 99.9 | 100.1 | ND | ND | ND | 100.4 | 100.3 | 99.5 | 100.2 | 100.3 | 99.9 | 99.9 |
| pH 7.0 | 97.5 | 99.2 | 100.6 | 99.8 | ND | ND | ND | ND | 99.7 | 99.8 | 99.3 | ND | ND | 0.2 | 99.7 | 99.9 | 100.0 | 99.9 | 99.9 | 99.4 | 99.7 |
| pH 7.5 | 96.8 | 99.6 | 100.1 | 100.2 | ND | ND | ND | ND | 99.5 | 99.8 | 98.7 | ND | 0.4 | 0.7 | 99.5 | 100.7 | 99.9 | 100.7 | 100.2 | 100.2 | 100.1 |
| pH 8.0 | 98.3 | 99.8 | 100.3 | 100.2 | ND | ND | ND | 0.2 | 99.2 | 98.7 | 97.0 | 0.5 | 0.9 | 1.8 | 100.2 | 100.6 | 100.2 | 100.5 | 100.1 | 100.2 | 99.7 |

FORMULATIONS FOR TREATING PAIN

CROSS-REFERENCE TO RELATED PATENT APPLICATIONS

This application claims priority to U.S. Provisional Patent Application Ser. No. 62/319,526, filed on Apr. 7, 2016 the contents of which are incorporated by reference in their entireties for all purposes.

TECHNICAL FIELD

Embodiments of the disclosure relate generally to formulations and methods of treating pain and, in particular, formulations comprising gabapentin or analogues of gamma-aminobutyric acid (GABA), optionally combined with at least one non-opioid pain drug.

BACKGROUND

Gabapentin, 1-(aminomethyl) cyclohexane acetic acid, is a structural analogue of the neurotransmitter gamma-aminobutyric acid. The oral absorption of gabapentin is dose-dependent due to a saturable L-amino acid transport mechanism in the intestine. Thus, the oral bioavailability varies inversely with dose. Following a dosing regimen of 900, 1200, 2400, 3600 and 4800 mg/day given in 3 divided doses, the bioavailability of gabapentin is approximately 60%, 47%, 33% and 27% respectively. Plasma concentrations are proportional with dose up to 1800 mg daily and then plateau at approximately 3600 mg daily.

Peroral administration of gabapentin to treat pain, for example in acute post-procedural pain relief, has been documented by various clinical studies. However, the peroral route has disadvantages, including uncertainty for use as pre-procedural medication. For example, gabapentin has a dose dependent extent of bio-availability, and oral absorption may be impaired because of loss of gastrointestinal function or restrictions on oral intake. For example, oral administration of gabapentin yields lower plasma concentrations because of its low bioavailability.

Accordingly, there is a need for an injectable pharmaceutical formulation comprising gabapentin or a derivative of gamma-aminobutyric acid for treating pain in general, including but not limited to post-procedural pain.

SUMMARY

In an embodiment, the present disclosure relates to formulations comprising gabapentin or a derivative of gamma-aminobutyric acid; in certain embodiments, the formulations further comprise at least one non-opioid pain drug in an aqueous carrier. The pharmaceutical formulation can have a pH of about 4.0 to about 8.0. In an embodiment, the derivative of gamma-aminobutyric acid is pregabalin. In another embodiment, the non-opioid pain drug is acetaminophen.

In other embodiments, the present disclosure provides methods of manufacturing a therapeutically effective injectable pharmaceutical formulation.

In other embodiments, the present disclosure provides methods of stabilizing a therapeutically effective injectable pharmaceutical formulation.

In other embodiments, the present disclosure provides kits comprising at least one dosage form comprising an injectable pharmaceutical formulation and instructions for administering the at least one dosage form.

In other embodiments, the present disclosure provides uses of gabapentin or a derivative of gamma-aminobutyric acid optionally combined with at least one non-opioid pain drug for preparation of a medicament to treat pain, wherein the medicament is administered by a dosing regimen.

BRIEF DESCRIPTION OF THE DRAWINGS

FIG. 1 provides Table 2 showing the stability of gabapentin in the presence of different stabilizers and solvents.

FIG. 2 provides Table 10 showing the stability of the acetaminophen and gabapentin formulation at different pH ranges (pH range 4.0-8.0).

DETAILED DESCRIPTION

Figure 3:
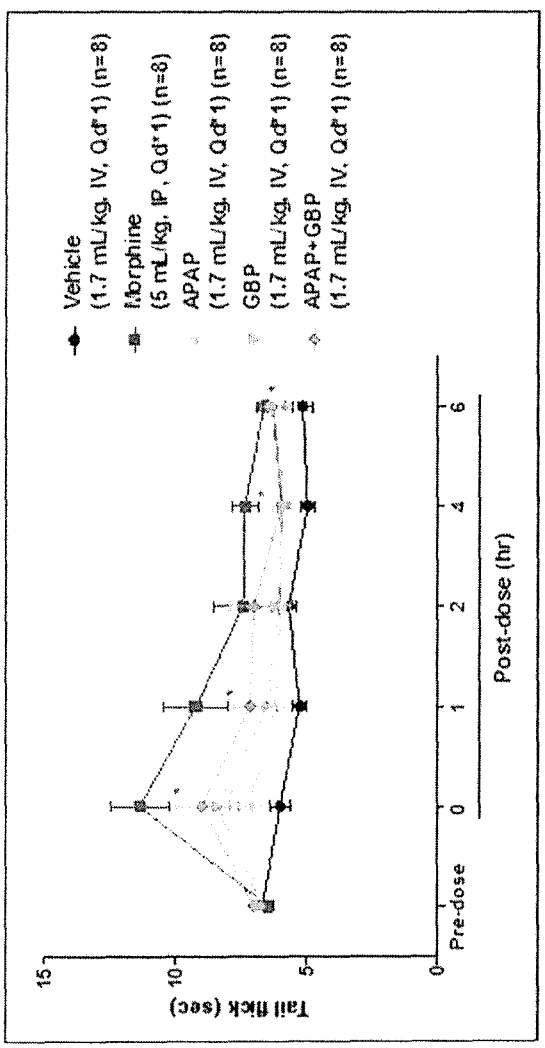
FIG. 3 provides a graph showing the results of a tail-flick test: the black circles (●) represent the vehicle, the square (■) represents morphine, the triangle (▲) represents acetaminophen, the inverted triangle (▼) represents gabapentin, and the diamond (♦) represents acetaminophen and gabapentin combined.

The following detailed description is exemplary and explanatory and is intended to provide further explanation of the present disclosure described herein. Other advantages, and novel features will be readily apparent to those skilled in the art from the following detailed description of the present disclosure.

The term "injectable infusion" should be construed to include different kinds of injectable delivery systems, including parenteral infusion, intravascular infusion, intra-arterial infusion, and intravenous infusion.

The term "formulation" should be construed to include an injectable infusion system comprising gabapentin, or a derivative of gamma-aminobutyric acid optionally combined with at least one non-opioid pain drug, and optionally a buffer, optionally an antioxidant, optionally a preservative, optionally a stabilizing agent, optionally an isotonicity adjusting agent, for parenteral delivery to a subject.

The term "pain" should be construed to include all forms and intensities of pain, including but not limited to acute pain, chronic pain, nociceptive pain, inflammatory pain, pathological pain, pre-surgical pain, surgical pain, post-surgical pain and neuropathic pain.

The term "procedure" should be construed to include different kinds of operations, including medical operations and surgical operations.

The term "subject" should be construed to include patients, for example medical or surgical patients, and other individuals suffering from pain, for example post-procedural pain.

To overcome the disadvantages of the conventional oral administration of gabapentin to treat pain, the inventors herein discovered an injectable pharmaceutical formulation comprising gabapentin or a derivative of gamma-aminobutyric acid optionally combined with at least one non-opioid pain drug for administration. The formulations may be administered at any time, including pre-procedure, peri-procedure, intra-procedure and/or post-procedure for treating pain, including post-procedural pain. As discussed above, there are disadvantages and uncertainties of oral absorption of gabapentin, including dose-dependent decrease in bioavailability. The inventors have discovered that these disadvantages can be solved by parenteral route of administration of a pharmaceutical formulation comprising gabapentin or a derivative of gamma-aminobutyric acid optionally combined with at least one non-opioid pain drug.

The pharmaceutical formulations of the present disclosure can achieve efficient and effective management of pain, including post-procedural pain. No such formulation is available in the market or reported in the literature.

Embodiments of the disclosure provide injectable pharmaceutical formulations and methods. In one embodiment, a formulation per the present disclosure comprises gabapentin or a derivative of gamma-aminobutyric acid optionally combined with at least one non-opioid pain drug in an aqueous carrier. In one embodiment, the derivative of gamma-aminobutyric acid is pregabalin. The aqueous carrier can be any aqueous carrier suitable for purposes of obtaining properties desirable for an injectable infusion, including, for example (without limitation), one or more of water, saline, lactated Ringer's solution, and Ringer's acetate solution.

In one embodiment, the non-opioid pain drug can be a non-steroidal anti-inflammatory drug. Suitable non-steroidal anti-inflammatory drugs for use in the present formulations and methods can comprise one or more of the following: acetaminophen, Aspirin (acetylsalicylic acid), Diflunisal, salicylic acid, salicylates, Salsalate, Ibuprofen, Dexibuprofen, Naproxen, Fenoprofen, Ketoprofen, Dexketoprofen, Flurbiprofen, Oxaprozin, Loxoprofen, indomethacin, Tolmetin, Sulindac, Etodolac, Ketorolac, Diclofenac, Aceclofenac, Nabumetone, Piroxicam, Meloxicam, Tenoxicam, Droxicam, Lornoxicam, Isoxicam, Phenylbutazone, Mefenamic acid, Meclofenamic acid, Flufenamic acid, Tolfenamic acid, Celecoxib and combinations thereof. In one embodiment, the non-opioid pain drug comprises acetaminophen.

In one embodiment, the pharmaceutical formulation can comprise one or more of the following: an antioxidant, a buffer, a preservative, a stabilizing agent, and an isotonicity adjusting agent. The buffer can be any buffer suitable for purposes of obtaining properties desirable for an injectable infusion, including, for example (without limitation), one or more of acetic acid, sodium acetate, citric acid, sodium hydroxide, cysteine hydrochloride, sodium dihydrogenphosphate, and disodium hydrogenphosphate. The buffer can be included in any amount suitable for purposes of obtaining properties desirable for an injectable infusion, for example in an amount of about 0.1 mM to 200 mM.

In one embodiment, the pharmaceutical formulation can be free from preservatives. In other embodiments, the pharmaceutical formulation can comprise one or more preservative agents suitable for purposes of obtaining properties desirable for an injectable infusion, including, for example (without limitation), one or more of quaternary ammonium salts, surfactant and disinfectant agents, for example benzalkonium chloride, cetremide or cetrimonium chloride or bromide, benzododecinium bromide, miramine, cetylpyridinium chloride, polidronium chloride or polyquartemium-1, polyquarternium-42 (also known as polexitonium), sepazonium, etc., mercurial derivatives, for example phenylmercury salts (acetate, borate or nitrate), mercuriothiolate sodium (otherwise called thiomersal or thimerosal), mercurobutol, amidines, for example chlorhexidine digluconate or polyhexamethylene biguanide (PHMB), alcohols, for example phenol, thimerosal, benzyl alcohol, phenoxyethanol, chlorobutanol or phenylethanol, phenoxyethanol, and parabens or esters, for example parahydroxybenzoic acid, methylparaben, and propylparaben. In one embodiment, the concentration of the preservatives is between about 0.001% w/w and less than about 5% w/w of the total composition, for example between about 0.003% and about 2.0% w/w of the total formulation.

In one embodiment, the pharmaceutical formulation can comprise one or more isotonicity agents suitable for purposes of obtaining properties desirable for an injectable infusion, including, for example (without limitation), sodium chloride, glycerol, and thioglycerol.

In one embodiment, the pharmaceutical formulation can comprise pharmaceutically acceptable excipients, for example one or more of buffers, preservatives, and antioxidants, and any pharmaceutically acceptable mixture thereof.

In one embodiment, the pharmaceutical formulation can be free from antioxidants. The inventors have unexpectedly discovered that pharmaceutical formulations according to the present disclosure with no antioxidants, and particularly with no N-acetyl cysteine, have increased stability.

In other embodiments, the pharmaceutical formulation can comprise one or more antioxidants suitable for purposes of obtaining properties desirable for an injectable infusion, including, for example (without limitation), one or more of hydrophobic anti-oxidants, for example butylated hydroxytoluene, butylated hydroxyanisole, propyl gallate, and α-tocopherol, DL-tocopherol, α-tocopherol acetate, Tocopherol Polyethylene Glycol Succinate (Vitamin E TPGS), L-cysteine, or hydrophilic anti-oxidants, including sodium EDTA and thioglycerol. In one embodiment, the concentration of the antioxidants is between 0.005% and 5% w/w of the total formulation. In one embodiment, the one or more antioxidants can improve the stability of the pharmaceutical formulation.

In one embodiment, the pharmaceutical formulation according to the present disclosure has a pH suitable for purposes of an injectable infusion. For example, the pH can be about 2.0 to about 10.0, about 4.0 and 8.0, or about 6.0 to about 7.0. In one embodiment, one or more buffer systems are used to stabilize the pH at a desired value or range. Suitable buffers include, for example (without limitation) citric acid buffer, acetic acid buffer, maleic acid buffer, phosphoric acid buffer, succinic acid buffer, and tartaric acid buffer. The buffer strength can be any buffer strength suitable for purposes of an injectable infusion, for example (without limitation) between about 0.1 mM to 200 mM.

In one embodiment, administration of the injectable pharmaceutical formulation according to the present disclosure to a subject occurs at least one of pre-procedure, peri-procedure, intra-procedure and/or post-procedure. In one embodiment, administration of the injectable pharmaceutical formulation to a subject is intravascular, for example intravenous. In one embodiment, administration of the injectable pharmaceutical formulation is to a subject having pain, including for example, post-procedural pain. In one embodiment, the pharmaceutical formulation according to the present disclosure treats post-procedural pain.

In one embodiment, the pharmaceutical formulation according to the present disclosure is packaged in a container. The container can be any container suitable for purposes of injectable infusion, including, for example (without limitation), a polymer bag, for example an infusion bag, or a glass bottle. In one embodiment, the polymer bag is further packaged in an aluminum over-wrap. In one embodiment, the polymer bag or aluminum over-wrap comprises an oxygen scavenger or an oxygen barrier. In another embodiment, an oxygen scavenger or oxygen barrier is between the polymer bag and the aluminum over-wrap or external to the aluminum over-wrap. In one embodiment, the pharmaceutical formulation according to the present disclosure comprises an aqueous solution comprising an oxygen scavenger.

In one embodiment, the polymer bag comprises a dual chamber bag. In this embodiment, the gabapentin or the derivative of gamma-aminobutyric acid is separated from the at least one non-opioid pain drug. The gabapentin or the derivative of gamma-aminobutyric acid can be separated from the at least one non-opioid pain drug by any suitable barrier. In another embodiment, the gabapentin or the derivative of gamma-aminobutyric acid and the non-opioid pain drug are in separate polymer bags, and can either be mixed in a single container prior to administration, or mixed during administration, for example by direction of both into a single IV line via a Y-connector.

The term "oxygen scavenger" or "oxygen barrier" should be construed to include a substance that consumes, depletes or reduces the amount of oxygen from a given environment without negatively affecting the pharmaceutical formulation. Suitable oxygen scavenging elements include, for example (without limitation) compositions comprising metal particulates reactive with oxygen such as transition metals selected from the first, second or third transition series of the periodic table of the elements, and include manganese II or III, iron II or III, cobalt II or III, nickel II or III, copper I or II, rhodium II, III or IV, and ruthenium, for example disposed within a polymer matrix that can be coated onto or incorporated into a container. The transition metal is, for example, iron, nickel or copper. Other examples of oxygen scavenging element may be enzymes which consumes, depletes or reduces the amount of oxygen from the given environment without negatively affecting the pharmaceutical formula.

In one embodiment, the pharmaceutical formulation according to the present disclosure comprises a 100 mL aqueous solution packaged in the polymer bag. In another embodiment, the pharmaceutical formulation according to the present disclosure comprises a 250 mL aqueous solution packaged in the polymer bag. In another embodiment, the pharmaceutical formulation according to the present disclosure comprises a 500 mL aqueous solution packaged in the polymer bag. In another embodiment, the pharmaceutical formulation according to the present disclosure comprises a 1000 mL aqueous solution packaged in the polymer bag.

In one embodiment, the gabapentin or the derivative of gamma-aminobutyric acid comprises a minimum of about 100 mg to about 2000 mg per container, for example about 500 mg to about 1000 mg, or from about 500 mg to 1500 mg. In one embodiment, the container optionally includes at least one non-opioid pain drug comprising a minimum of about 100 mg to about 2000 mg per container, for example about 500 mg to about 1000 mg, or about 500 mg to about 1500 mg.

In one embodiment, the concentration of the gabapentin or the derivative of gamma-aminobutyric acid is less than about 99% (w/v) and the concentration of the optional non-opioid pain drug concentration is less than about 99% (w/v). The concentration of the gabapentin or the derivative of gamma-aminobutyric acid can be about 1 to 200 mg/mL and the concentration of the optional non-opioid pain drug can be about 1 to 200 mg/mL. In another embodiment, the concentration of the gabapentin or the derivative of gamma-aminobutyric acid can be about 1 to 400 mg/mL and the concentration of the optional non-opioid pain drug can be about 1 to 400 mg/mL.

In one embodiment, the single dose of the pharmaceutical formulation described herein comprises gabapentin, or a derivative of gamma-aminobutyric acid, in the amount of 100-1200 mg, 400-1000 mg, 400 mg, or 800 mg. In an embodiment, the single dose of the pharmaceutical formulation described herein comprises gabapentin, or a derivative of gamma-aminobutyric acid, in the amount of 100-1200 mg, 400-1000 mg, 400 mg, or 800 mg, optionally combined with a non-opioid pain drug in the amount of in the amount of 100-2000 mg, 400-1600 mg, 800 mg, or 1000 mg. In an embodiment, the single dose of the pharmaceutical formulation described herein comprises gabapentin, in the amount of 100-1200 mg, 400-1000 mg, 400 mg, or 800 mg combined with a non-opioid pain drug in the amount of in the amount of 100-2000 mg, 400-1600 mg, 800 mg, or 1000 mg, wherein the non-opioid drug comprises acetaminophen.

In one embodiment, the pharmaceutical formulations of the present disclosure are sterilized by any means of sterilization suitable for purposes of injectable infusion, including, for example (without limitation), filtration through 0.22 micron filters, steam sterilization, radiation (e.g., gamma, electron beam, microwave), or ethylene oxide sterilization.

In one embodiment, an injectable infusion comprising the pharmaceutical formulations according to the present disclosure can have desirable properties, including, for example (without limitation) desirable stability properties, pharmacokinetic properties, and bioavailability. One skilled in the art can readily determine the stability properties of the present formulations, for example by employing standard testing procedures. For example, stability samples can be assayed for lactam and gabapentin by an HPLC procedure as set forth in *Pharmaceutical Research, Vol. 9, No. 5, 1992, Stability Studies of Gabapentin in Aqueous Solutions* by E. Zour, et al., the entire disclosure of which is herein incorporated by reference. In this procedure, the HPLC system uses a diode array detector. The samples are assayed on a reversed-phase B C18 Ultrashpere ODS 5-μm, 4.6 mm×25-cm, column. The mobile phase comprises of a water-methanol-acetonitrile (55:35:10) mixture and the flow rate can be 1.0 ml/min. The detection is carried out at 210 nm. All samples assayed are diluted 10-fold and then 50 μl of the sample is injected into the HPLC system. In one embodiment, HPLC retention times of gabapentin and lactam are found to be about 3.1 and about 13.3 min. Initial studies indicated that at neutral pH, gabapentin or derivatives of gamma-aminobutyric acid have an aqueous shelf life of about 2 to about 6 months at room temperature (25° C.), with a lactam limit of about 0.5%. Formulations of the present invention have a shelf-life of about 4-24 months at room temperature, for example about 18 to 24 months, and this can be longer, and lactam limits of about 0.5% and this can be less.

In another example, high-performance liquid chromatography (HPLC) method can been used for the simultaneous determination of the main impurities of the non-opioid pain drug. For example, HPLC can be used for simultaneous determination of the main impurities of acetaminophen, including for example n-propionyl-p-aminophenol, 3-chloro-4-hydroxyacetanilide, 4'-hydroxyacetophenone, 4-hydroxyacetophenone oxime, 4-acetoxyacetanilide and 4'-chloroacetanilid, as set forth in *Journal of Chromatographic Science, Vol.* 50:335-342, 2012, *HPLC Separation of Acetaminophen and its Impurities Using a Mixed-mode Reversed-Phase/Cation Exchange Stationary Phase*, by O. Calinescu, et al., the entire disclosure of which is herein incorporated by reference. The chromatographic separation can be achieved on an Eclipse XDB-18 reversed-phase column using a gradient elution, with solvent A: 0.01 M phosphate buffer at pH 3.0 and solvent B: methanol. Levels of these impurities in the present formulations are well within acceptable limits, as are known in the art.

In one embodiment, parenteral administration of the pharmaceutical formulation achieves a bioavailability of the gabapentin or the derivative of gamma-aminobutyric acid of about 20% to about 100% and elimination half-life of the gabapentin or the derivative of gamma-aminobutyric acid is about 4 to about 8 hours. In one embodiment, parenteral administration of the pharmaceutical formulation achieves a bioavailability of gabapentin or the derivative of gamma-aminobutyric acid that is higher than a bioavailability achieved by oral administration. In one embodiment, parenteral administration of the pharmaceutical formulation achieves an elimination half-life of gabapentin or the derivative of gamma-aminobutyric acid that is longer than elimination half-life achieved by oral administration.

In one embodiment, methods of manufacturing a therapeutically effective injectable pharmaceutical formulation are provided. The methods can comprise dissolving gabapentin or a derivative of gamma-aminobutyric acid optionally combined with at least one non-opioid pain drug in an aqueous carrier, and adjusting a pH of the pharmaceutical formulation to about 4.0 to about 8.0. The formulation can comprise one or more formulations as described above.

In one embodiment, methods of stabilizing a therapeutically effective injectable pharmaceutical formulation are provided. The methods can comprise dissolving gabapentin or a derivative of gamma-aminobutyric acid optionally combined with at least one non-opioid pain drug in an aqueous carrier, dissolving a buffer in the aqueous carrier, and adjusting a pH of the pharmaceutical formulation to about 4.0 to about 8.0 using the buffer. The formulation can comprise one or more formulations as described above. Stability of the formulations can be determined by any suitable means known in the art, for example those methods described above.

In one embodiment, kits comprising at least one dosage form comprising an injectable pharmaceutical formulation and instructions for administering the at least one dosage form are provided. The formulation can comprise one or more formulations as described above. The therapeutic instructions can comprise the step of intravascularly administering to a subject who has pain the pharmaceutical formulation.

In one embodiment, uses of gabapentin or a derivative of gamma-aminobutyric acid optionally combined with at least one non-opioid pain drug for preparation of a medicament to treat post-procedural pain, wherein the medicament is administered by a dosing regimen, are provided. The dosing regimen can comprise intravascularly, for example intravenously, administering to a subject who has pain an injectable pharmaceutical formulation. The formulation can comprise one or more formulations as described above.

The dosage of the present formulations provided to a subject will vary depending upon the active ingredients being administered, the purpose of the administration, such as prophylaxis or therapy, and the state of the subject and/or level of pain, the manner of administration, and the like. In therapeutic applications, formulations described herein are provided to a subject already suffering from pain, in an amount sufficient to at least partially ameliorate the symptoms of the pain and/or its complications, including, for example (without limitation) post-procedural pain. An amount of present formulations comprising an active ingredient adequate to accomplish this is defined as a "therapeutically effective amount." The dosage to be used in the treatment of a specific case must be subjectively determined by and would be apparent to the ordinarily skilled physician or medical professional. The variables involved for determining a therapeutically effective amount of the present formulations include the specific condition and the size, age, weight, gender, disease penetration, type of procedure, and response pattern of the subject. The compounds can be administered intravascularly, for example intravenously. The present formulations can be provided as a unit dose, for example as an infusion, which taken together comprise a therapeutically effective amount. For example, a unit dose comprising a formulation of the invention can be administered once daily or multiple times daily, for example 1, 2, 3, 4, 5 or 6 times in a 12 or 24-hour period. If multiple unit doses are administered in a given time period, they can be administered at substantially even time intervals. For example, if two unit doses are administered in a 12-hour period, they can be given to the subject 6 hours apart. Multiple unit doses are administered in a given time period can also be administered at substantially uneven time intervals. In one embodiment, a unit dosage form comprises a formulation of the invention in the form of an injectable infusion for intravenous administration.

The usual daily (i.e., 24-hour time period) dose depends on the specific compound, method of treatment and condition treated. The usual daily dose for the gabapentin or derivative of gamma-aminobutyric acid is about 1 to 500 mg/mL for parenteral application, for example 8 mg/mL, and for the at least one non-opioid pain drug is about 1 to 500 mg/mL for parenteral application, for example 10 mg/mL.

In an embodiment, a pharmaceutical formulation of the present disclosure comprises gabapentin, acetaminophen; in an aqueous carrier, wherein the pharmaceutical formulation has a pH of about 5.0 to about 7.0, and wherein a concentration of the gabapentin is about 5 to 15 mg/mL and a concentration of the acetaminophen is about 5 to 15 mg/mL wherein such a formulation is suitable for intravenous administration and wherein such a formulation is useful for the treatment of pain.

The following examples are given to illustrate exemplary embodiments of the present disclosure. It should be understood, however, that the present disclosure is not to be limited to the specific conditions or details described in these examples.

EXAMPLES

In the Following Examples, "GBP" is Used to Mean Gabapentin, and "APAP" is Used to Mean Acetaminophen Example 1

Composition of Gabapentin (GBP) Formulation in Water for Injection and Buffered Vehicles Required quantities of Water for injection (WFI) were combined with Citrate Phosphate Buffer (10 mM), and Acetate Buffer (10 mM) in three separate manufacturing tanks. Gabapentin (GBP) was added to each of tanks to obtain a concentration of 10 mg/ml, and the pH was readjusted to 5.5 using HCl or NaOH. The bulk solution tanks were filled into 10 mL glass vials with a target fill volume of 10 mL and then stoppered and sealed. Samples were tested for assay and impurities. Samples were steam sterilized at 121° C. for 15 min and were analyzed for assay and impurity levels.

TABLE 1

| | Gabapentin Formulations | | |
|---|---|---|---|
| | Example A Water for injection (WFI) | Example B Citrate Phosphate Buffer (10 mM) | Example C Acetate Buffer (10 mM) |
| Ingredients | | Amount/mL (mg) | |
| Gabapentin | | 10 | |
| Sodium Hydroxide | | q.s. | |
| Hydrochloric Acid | | q.s. | |
| Vehicle | | q.s. 1 mL | |
| pH | | 5.5 | |

| | GBP | Lactam | GBP | Lactam | GBP | Lactam |
|---|---|---|---|---|---|---|
| Assay (T0) (%) | 102.0 | ND | 102.3 | ND | 101.7 | ND |
| Post Sterilization (%) | 97.4 | 3.30 | 96.8 | 3.85 | 95.6 | 4.08 |

Data in Table 1 demonstrates that unbuffered gabapentin (10 mg/mL) at pH of about 5.5 had significantly higher assay and lower level of impurity compared to gabapentin in presence of citrate and acetate buffer.

Example 2

Composition of Gabapentin (GBP) Formulation in Presence of Different Stabilizers and Solvents GBP containing formulations were prepared by dissolving GBP to a concentration of 9 mg/mL in acetate buffer. Additional stabilizers and solvents were added as indicated in Table 2 below. A first set of samples were tested for assay and impurities after the initial preparation of formulation. Another set of samples were steam sterilized at 121° C. for 15 min and were tested for assay and impurity levels.

As shown in Table 2 (FIG. 1), GBP was found to be more stable in solutions containing polyvinyl pyrrolidone (PVP) at a concentration of 10 mg/mL. Table 2 also depicts the stability of GBP in other solvents and stabilizers in the following order: PVP>Glycine>Lysine>Propylene Glycol>Sorbitol>PEG400>Glycerol>Mannitol>Sodium Oleate>β-cyclodextrin>Deoxychloic Acid>CMC>L-Glutamic Acid.

Example 3

Stability of GBP, APAP and APAP+GBP Formulation at pH 5.5

Formulation compositions were prepared by dissolving GBP and/or APAP as indicated in Table 3 and 4 and the pH was adjusted to 5.5 using HCl or NaOH.

TABLE 3

| | Stability of APAP, GBP and APAP + GBP formulations in water for injection at pH 5.5 | | |
|---|---|---|---|
| | Q | R | S |
| | | Water for injection (WFI) | |
| Ingredients | Amount/mL (mg) | Amount/mL (mg) | Amount/mL (mg) |
| Gabapentin | 9 | | 9 |
| Acetaminophen | | 10 | 10 |
| Sodium Hydroxide | q.s. pH 5.5 | q.s. pH 5.5 | q.s. pH 5.5 |
| Hydrochloric Acid | q.s. pH 5.5 | q.s. pH 5.5 | q.s. pH 5.5 |
| Vehicle | q.s. 1 mL | q.s. 1 mL | q.s. 1 mL |

| | GBP | Lactam | APAP | GBP | Lactam | APAP |
|---|---|---|---|---|---|---|
| Assay (T0) (%) | 99.1 | ND | 100.2 | 102.3 | ND | 101.2 |
| Assay 2 Month (%) | 97.6 | ND | 100.4 | 99.1 | ND | 101.3 |

TABLE 4

| | Stability of APAP, GBP and APAP + GBP formulations in acetate buffer at pH 5.5 | | |
|---|---|---|---|
| | T | U | V |
| | | Acetate Buffer (10 mM) | |
| Ingredients | Amount/mL (mg) | Amount/mL (mg) | Amount/mL (mg) |
| Gabapentin | 9 | | 9 |
| Acetaminophen | | 10 | 10 |
| Sodium Hydroxide | q.s. pH 5.5 | q.s. pH 5.5 | q.s. pH 5.5 |

TABLE 4-continued

Stability of APAP, GBP and APAP + GBP formulations in acetate buffer at pH 5.5

| Hydrochloric Acid | q.s. pH 5.5 | | | q.s. pH 5.5 | | | q.s. pH 5.5 | | |
|---|---|---|---|---|---|---|---|---|---|
| Vehicle | q.s. 1 mL | | | q.s. 1 mL | | | q.s. 1 mL | | |
| | GBP | Lactam | APAP | GBP | Lactam | APAP | | | |
| Assay (T0) (%) | 100.6 | ND | 101.6 | 101.8 | ND | 101.8 | | | |
| Assay 2 Month (%) | 98.0 | ND | 101.0 | 96.6 | ND | 100.7 | | | |

As can be seen from Tables 3 and 4 above, all the three formulations were stable for up to 2 months at 25° C. No significant difference in stability of formulations were observed in formulations prepared in water for injection or acetate buffer. Generation of lactam impurity was not observed in either of the formulation sets prepared with water for injection or acetate buffer.

Example 4

Pharmacokinetics and Toxicologic Profile in Rats for Acetaminophen, Gabapentin Alone or in Combination Formulation compositions were prepared by dissolving GBP and/or APAP as indicated in Table 5 and the pH was adjusted to 5.5 using HCl or NaOH. As observed in the previous study acetate buffer does not play any role in stabilizing the formulation, therefore the formulation compositions mentioned in Table 5 were prepared without use of acetate buffer.

Male rats were administered Acetaminophen (10 mg/mL) or Gabapentin (8 mg/mL) alone or in combination with a vehicle control to evaluate the pharmacokinetic and toxicologic profile over a 24 h period following a 15 minute IV infusion. Blood samples were collected over a 24 h period at which time the rats were exsanguinated and blood collected for Clinical Pathology (Chemistry, Hematology and Coagulation) evaluation. Finally, all animals were necropsied (all exterior and interior cavities and organs were examined) and the site of infusion in the jugular vein, lung, liver and kidney underwent histopathologic evaluation.

TABLE 5

Composition of APAP, GBP and APAP + GBP formulations employed for in vivo studies.

| | W | X | Y |
|---|---|---|---|
| | | Water for injection (WFI) | |
| Ingredients | Amount/mL (mg) | Amount/mL (mg) | Amount/mL (mg) |
| Gabapentin | 8 | | 8 |
| Acetaminophen | | 10 | 10 |
| Sodium Hydroxide | q.s. | q.s. | q.s. |
| Hydrochloric Acid | q.s. | q.s. | q.s. |
| Vehicle | q.s. 1 mL | q.s. 1 mL | q.s. 1 mL |
| pH | 5.5 | 5.5 | 5.5 |

TABLE 6

Pharmacokinetic (PK) parameters observed after 15 min infusion of APAP, GBP and APAP + GBP formulations in rats.

| | Acetaminophen PK | | Gabapentin PK | | Bioequivalent Range (80-125%) | |
|---|---|---|---|---|---|---|
| Group | $C_{max}$ (ng/mL) | AUC (ng · h/mL) | $C_{max}$ (ng/mL) | AUC (ng · h/mL) | $C_{max}$ (ng/mL) | AUC (ng · h/mL) |
| Saline | 0 | 0 | 0 | 0 | | |
| Acetaminophen | 10,135 | 7,285 | | | 8,108-12,669 | 5,828-9,106 |
| Gabapentin | | | 20,138 | 37,663 | | |
| APAP + GBP | 13,550 | 8,526 | 20,029 | 42,701 | 16,110-25,172 | 30,130-47,079 |

Results from this study demonstrate that treatment of rats with either acetaminophen or gabapentin alone or in combination in this formulation did not alter the Clinical Pathology (Clinical Chemistry, Hematology or Coagulation Parameters) for these animals. Further there were no changes in the histopathology in any tissue sampled compared to the vehicle control.

PK parameters were analyzed after 15 min infusion of APAP, GBP and APAP+GBP formulations in rats. Maximal plasma concentration of acetaminophen ($C_{max}$) obtained for APAP+GBP combination formulation was found to be 30% higher when compared with $C_{max}$ obtained after administering APAP alone. Whereas no change was observed in PK profile of GBP in the presence of APAP. The combination of APAP and GBP did not alter the total exposure (AUC, Area Under the Curve) compared to either drug given alone.

Results from this study demonstrate that under the conditions of this study this new formulation of APAP+GBP does not induce hemolysis of rat blood, alter clinical pathology parameters, nor induce changes in key tissues in the rats (infusion site, lung, liver, kidney and brain).

Example 5

Solubility Studies of APAP, GBP and APAP+GBP at Different pH (pH Range 4.0-8.0)

Solubility samples were prepared by dissolving APAP in water at 50 mg/mL concentration and adjusting the pH in the required range. As can be seen from Table 7 no significant difference in solubility of APAP was observed in the overall pH range from 4.0-8.0.

TABLE 7 pH dependent solubility studies of APAP + GBP at different pH range (4.0-8.0)

| Sample | Acetaminophen(mg/mL) |
|---|---|
| pH 4.0 | 13.8 |
| pH 4.5 | 14.1 |
| pH 5.0 | 13.9 |
| pH 5.5 | 13.9 |
| pH 6.0 | 13.8 |
| pH 6.5 | 13.9 |
| pH 7.0 | 13.9 |
| pH 7.5 | 13.9 |
| pH 8.0 | 14.2 |

TABLE 8 pH dependent solubility studies of GBP at different pH range (4.0-8.0)

| Sample | Gabapentin (mg/mL) |
|---|---|
| pH 4.0 | 129.2 |
| pH 4.5 | 125.8 |
| pH 5.0 | 106.1 |
| pH 5.5 | 101.3 |
| pH 6.0 | 99.5 |
| pH 6.5 | 97.5 |
| pH 7.0 | 99.0 |
| pH 7.5 | 98.6 |
| pH 8.0 | 98.7 |

Saturation solubility samples were prepared by addition of 150 mg/mL of GBP in water and adjusting the pH in the required range. As can be seen from Table 8 solubility of GBP was higher at lower pH range (4.0-5.0) and was found to ~98 mg/ml at the pH range of 6.0-8.0.

TABLE 9 pH dependent solubility studies of APAP + GBP at different pH range (4.0-8.0)

| Sample | Acetaminophen (mg/mL) | Gabapentin (mg/mL) |
|---|---|---|
| pH 4.0 | 32.9 | 125.7 |
| pH 4.5 | 31.7 | 129.8 |
| pH 5.0 | 30.7 | 126.7 |
| pH 5.5 | 30.2 | 124.1 |
| pH 6.0 | 28.8 | 120.0 |
| pH 6.5 | 28.4 | 117.4 |
| pH 7.0 | 30.5 | 122.3 |
| pH 7.5 | 27.8 | 122.9 |
| pH 8.0 | 31.3 | 123.0 |

Solubility samples were prepared by dissolving APAP and GBP in water at 50 and 150 mg/mL concentration, respectively and adjusting the pH in the required range. As can be seen from Table 9, solubility of APAP solubility was increased to ~30 mg/mL in presence of GBP which is more than twice the solubility values obtained all the same pH range for APAP alone (Table 7).

Also significant increase in the solubility of GBP in presence of APAP was also observed at pH range of 5.0-8.0 in comparison to solubility values obtained in the same pH range for GBP alone (Table 8).

Example 6

Stability of APAP+GBP Formulation at Different pH (pH Range 4.0-8.0)

Formulation compositions were prepared by dissolving APAP and GBP in water at 10 and 8 mg/mL concentration, respectively and adjusting the pH in the required range.

As can be seen from Table 10 (FIG. 2), lactam impurity generated in 1 month stability samples were well below the specifications (<0.5%) at pH 5.5-7.0 (40° C./75% RH). Also, lactam impurity was not detected in 1 month stability samples at pH 5.5-7.5 (40° C./75% RH). It is known that APAP undergoes hydrolytic degradation to form para-aminophenol. The mechanism involving hydrolysis was proposed by Koshy K. T. et al (J Pharm Sci. 1961 February; 50:113-8). Koshy et al has reported that the hydrolysis of APAP is minimum in the pH range 5 to 7 and it is desirable to keep the pH of the medium between 5 and 6 to obtain maximum shelf life for the APAP product. As reported in Table 10, APAP assay values obtained at pH 5.0-6.0 were ~100% and low lactam impurity levels (<0.5%) were obtained for GBP around the same pH range (5.0-6.0). Hence, the pH of 5.5 was selected for APAP+GBP formulation prepared for future studies.

Example 7

In Vitro Hemolysis of Formulation of Acetaminophen, Gabapentin Alone or in Combination APAP and GBP alone or in combination were evaluated in the in vitro hemolysis test using four biologic matrices (mouse, rat, dog and human whole unclotted blood) to determine the hemolytic potential for each on red blood cells. Blood was mixed with either Acetaminophen (2.5, 5, 10 mg/mL), Gabapentin (2, 4, 8 mg/kg) or the combination, along with a saline control and positive control (2% SDS) and incubated for 15 min at 37° C.

TABLE 11

Detection of hemolysis in mouse whole blood (male), rat whole blood (male), beagle dog whole blood (male), human (pooled) whole blood

| Species | GBP (2 mg/mL) | GBP (4 mg/mL) | GBP (8 mg/mL) |
|---|---|---|---|
| | % Hemolysis | | |
| Mouse Blood | 0 | 0 | 0 |
| Rat Blood | 0 | 0 | 0 |
| Dog Blood | 0 | 0 | 0 |
| Human Blood | 0 | 2 | 0 |

| Species | APAP (2.5 mg/mL) | APAP (5 mg/mL) | APAP (10 mg/mL) |
|---|---|---|---|
| | % Hemolysis | | |
| Mouse Blood | 3 | 4 | 4 |
| Rat Blood | 2 | 0 | 0 |

TABLE 11-continued

Detection of hemolysis in mouse whole blood
(male), rat whole blood (male), beagle dog whole
blood (male), human (pooled) whole blood

| | | | |
|---|---|---|---|
| Dog Blood | 0 | 0 | 5 |
| Human Blood | 0 | 0 | 0 |

| Species | APAP (10 mg/mL) + GBP (2 mg/mL) | APAP (10 mg/mL) + GBP (4 mg/mL) % Hemolysis | APAP (10 mg/mL) + GBP (8 mg/mL) |
|---|---|---|---|
| Mouse Blood | 0 | 2 | 0 |
| Rat Blood | 0 | 0 | 2 |
| Dog Blood | 2 | 0 | 1 |
| Human Blood | 4 | 2 | 0 |

TABLE 12

Criteria for Determination of Hemolysis

| Percent Hemolysis | Interpretation |
|---|---|
| <10% | Not Hemolytic |
| 10%-25% | Relative Boundary (Possibly Hemolytic) |
| >25% | Hemolytic |

Based on the results of this study (Table 11 and 12), in the current formulation and concentrations tested, APAP and GBP alone or in combination were not considered to be hemolytic to Red Blood Cells under the conditions tested (15 min at 37° C.) in mouse, rat, dog or human whole unclotted blood.

Example 8

Pharmacodynamic Parameters in Mice for Acetaminophen, Gabapentin Alone or in Combination Two pharmacodynamic parameters were evaluated in the mouse model to evaluate the effects of Acetaminophen (1000 mg/dose), Gabapentin (800 mg/dose) and the combination. Mouse tail flick test was conducted to evaluate test somatic pain and mouse rotorod/acelorod test evaluated behavioral changes, specifically somnolence or dizziness A negative control (vehicle) and the test agents (Acetaminophen, Gabapentin or the combination) were administered by an IV route 30 minutes before the initiation of testing. In each case a positive control was administered as described below.

A. Tail-Flick Test:

The test evaluates somatic pain by measuring the time (seconds) required to elicit a tail flick response induced by focused radiant heat. A 15-sec cut-off is used to prevent tissue damage. The study evaluated baseline measurements (before dosing) and at 30 minutes before the initiation of the study (time 0) the mice were administered a 15-minute IV infusion of either the Vehicle, Acetaminophen (10 mg/mL), Gabapentin (8 mg/mL) or the combination at a dose of 1.7 mL/kg. The positive control, Morphine (0.6 mg/kg, 5 mg/kg by the IP route) 30 minutes prior to the initiation of the study. The measurements were conducted at 1, 2, 4, and 6 hours after the initiation of the study FIG. 1. One-way ANOVA followed by Dunnett's test is applied for comparison between vehicle control and test article treated groups. $P<0.05$ is considered significant.

Results from this study indicate that the combination of Acetaminophen and gabapentin in the current formulation are superior to either compound alone under the conditions of this study.

As shown in FIG. 3, Mice were administered either Vehicle, Acetaminophen (10 mg/mL), Gabapentin (8 mg/mL) or a combination of the two test agents by a 15 minute IV infusion 30 minutes before the start of the study. A baseline was measured before administration of the test agents and at 1, 2, 4 and 6 h post the start of the study. The effect of the compounds was evaluated in the standard Tail-Flick test.

(B) RotoRod/Acelerorod Test:

Male ICR mice were trained on a RotoRod/Acelerod at a continuous accelerating speed from 4 to 30 rpm/min during a time period of 4 minutes for at least 3 times on day 0. Vehicle or test article at a single dose is administered by intravenous infusion over 15 minutes starting 30 minutes before the test period starts and chlorpromazine (30 mg/kg, PO) was administered by oral gavage 60 minutes before the start of the test period. At 1, 2, 4, and 6 hours after the start of the test the mice are placed on the accelerating rotorod (increasing from 4 to 30 rpm/min during a 4 min period) and the time (seconds) the mouse remained on the rotorod was recorded. One-way ANOVA followed by Dunnett's test is applied for comparison between vehicle control and test article groups. $P<0.05$ is considered significant.

Results from this study indicate that at a dose of 10 mg Acetaminophen/mL, or 8 mg Gabapentin/mL or in combination, there was no statistically significant decrease in motor control compared to the vehicle control (see FIG. 4).

As shown in FIG. 4, Mice were administered either Vehicle, Acetaminophen (10 mg/mL), Gabapentin (8 mg/mL) or a combination of the two test agents by a 15 minute IV infusion 30 minutes before the start of the study. A baseline was measured before administration of the test agents and at 1, 2, 4 and 6 h post the start of the study. The effect of the compounds was evaluated in the standard RotoRod/Acelerorod test.

Table 5 below provides a list of exemplary non-opioid pain drugs for use in pharmaceutical formulations according to the present disclosure, including exemplary daily dosage in mg. These non-opioid pain drugs in the following total amounts can be substituted into the formulations of Examples above.

TABLE 5

Exemplary non-opioid pain drugs

| NSAID | Daily Dose |
|---|---|
| Aspirin | 250 mg |
| Ibuprofen | 800 mg |
| Naproxen | 500 mg |
| Indomethacin | 15 mg |
| Ketorolac | 120 mg |
| Diclofenac | 150 mg |
| Meloxicam | 15 mg |
| Celecoxib | 200 mg |
| Mefenamic acid | 500 mg |
| Acetaminophen | 4000 mg |

While the present disclosure has been discussed in terms of certain embodiments, it should be appreciated that the present disclosure is not so limited. The embodiments are explained herein by way of example, and there are numerous modifications, variations and other embodiments that may be employed that would still be within the scope of the present disclosure.

The invention claimed is:

1. An injectable pharmaceutical formulation comprising: gabapentin and acetaminophen; in an aqueous carrier, wherein the pharmaceutical formulation has a pH of about 5 to about 6.

2. The pharmaceutical formulation of claim 1, further comprising a buffer, or a tonicity inducing agent.

3. The pharmaceutical formulation of claim 1, wherein the pharmaceutical formulation has a pH of about 5.5.

4. The pharmaceutical formulation of claim 1, wherein the pharmaceutical formulation is formulated for packaging in a bag.

5. The pharmaceutical formulation of claim 4, wherein the bag is a polymer bag, and the polymer bag is further packaged in an aluminum over-pouch.

6. The pharmaceutical formulation of claim 5, wherein the aluminum over-pouch comprises an oxygen scavenger.

7. The pharmaceutical formulation of claim 4, wherein the bag contains from about 15 mg to about 4000 mg of gabapentin.

8. The pharmaceutical formulation of claim 4, wherein the bag contains about 100 mg to about 4000 mg of acetaminophen.

9. The pharmaceutical formulation of claim 1, wherein a concentration of the gabapentin in the pharmaceutical formulation is less than about 99% (w/v) and wherein a concentration of acetaminophen in the pharmaceutical formulation is less than about 99% (w/v).

10. The pharmaceutical formulation of claim 1, wherein a concentration of the gabapentin in the pharmaceutical formulation is about 1 to 50 mg/mL and a concentration of acetaminophen in the pharmaceutical formulation is about 1 to 50 mg/mL.

11. The pharmaceutical formulation of claim 1, wherein the aqueous carrier is selected from the group consisting of water, saline, an aqueous mannitol formulation, lactated Ringer's solution, and Ringer's acetate solution.

12. The pharmaceutical formulation of claim 1, wherein gabapentin is present in the pharmaceutical formulation at a concentration of about 1 mg/mL to about 8 mg/mL.

13. The pharmaceutical formulation of claim 1, wherein acetaminophen is present in the pharmaceutical formulation at a concentration of about 10 mg/mL.

14. The pharmaceutical formulation of claim 1, wherein the concentration of the gabapentin in the pharmaceutical formulation is about 1 to 200 mg/mL and the concentration of acetaminophen in the pharmaceutical formulation is about 1 to 400 mg/mL.

15. The pharmaceutical formulation of claim 1, wherein the pharmaceutical formulation further comprises a pH stabilizer, wherein gabapentin is present in the pharmaceutical formulation at a concentration of about 8 mg/mL, and acetaminophen is present in the pharmaceutical formulation at a concentration of about 10 mg/mL, wherein the pharmaceutical formulation has a pH of about 5.5.

16. The pharmaceutical formulation of claim 1, wherein the pharmaceutical formulation does not comprise an antioxidant.

17. The pharmaceutical composition of claim 1, wherein the pharmaceutical formulation exhibits no more than about 0.5% of a lactam impurity after storage at about 25° C. for about one month.

* * * * *